United States Patent [19]

Bolick

[11] 4,315,508
[45] Feb. 16, 1982

[54] SELF-CENTERING MULTIPLE USE GARMENT SUSPENSION SYSTEM

[75] Inventor: Martha E. Bolick, Neenah, Wis.

[73] Assignee: Kimberly-Clark Corporation, Neenah, Wis.

[21] Appl. No.: 135,536

[22] Filed: Mar. 31, 1980

[51] Int. Cl.³ ............................................. A61F 13/16
[52] U.S. Cl. ..................................................... 128/289
[58] Field of Search ............... 128/284, 286, 287, 288, 128/289, 290 R, 290 H, 291; 24/16 PB, 17 B, 73 BG, 202.1; 428/288

[56] References Cited

U.S. PATENT DOCUMENTS

| | | | |
|---|---|---|---|
| 1,998,140 | 4/1935 | Loew . | |
| 2,011,027 | 8/1935 | Ballard et al. | 128/289 |
| 2,062,978 | 12/1936 | King | 128/284 |
| 2,206,412 | 7/1940 | Levy . | |
| 2,272,830 | 2/1942 | Brody et al. . | |
| 2,408,723 | 10/1946 | Arpin et al. . | |
| 2,419,867 | 4/1947 | Woodman . | |
| 2,596,127 | 5/1952 | Carmean | 128/288 |
| 2,739,595 | 3/1956 | Huggins | 128/295 |
| 2,798,489 | 7/1957 | Behrman | 128/283 |
| 3,059,644 | 10/1962 | Atkinson | 128/290 R |
| 3,094,990 | 6/1963 | Neilson | 128/289 |
| 3,315,324 | 4/1967 | Ward | 24/16 PB |
| 3,452,753 | 7/1969 | Sanford | 128/287 |
| 3,494,361 | 2/1970 | Thivat | 128/287 |
| 3,774,610 | 11/1973 | Eckert et al. | 128/287 |
| 3,800,796 | 4/1974 | Jacob | 128/284 |
| 3,834,824 | 10/1974 | Jahn | 24/16 PB |
| 3,882,870 | 5/1975 | Hathaway | 128/284 |
| 3,920,018 | 11/1975 | Schaar | 128/290 R |
| 4,067,336 | 1/1978 | Johnson | 128/284 |
| 4,100,324 | 7/1978 | Anderson et al. | 428/288 |
| 4,182,334 | 1/1980 | Johnson | 128/287 |

FOREIGN PATENT DOCUMENTS

| | | | |
|---|---|---|---|
| 318440 | 9/1929 | United Kingdom | 128/289 |
| 434980 | 9/1935 | United Kingdom | 128/289 |

Primary Examiner—C. Fred Rosenbaum
Attorney, Agent, or Firm—William D. Herrick; W. K. Fredericks; H. Olevsky

[57] ABSTRACT

Suspension system intended primarily for disposable items such as incontinent pads, disposable diapers, and the like but having other uses as well. The garment is intended to be worn about the crotch area and generally is rectangular in shape although various fold configurations in the crotch area may be utilized for improved comfort and fit. The suspension system includes two elastic strips of generally similar construction and having dimensions selected in accordance with the invention to provide the self-centering and improved comfort and fit features. The ends of the elastic strips are provided with buttons or other fastening means intended to cooperate with means provided in the garment material so that, in use, the elastic provides a vertical vector of force maintaining the garment snugly in place. Preferably the straps in use form an angle in the range of from 25° to 45° from horizontal when viewed from a standing frontal position. Garments of the invention provide self-centering characteristics and close fit to the perineal area resulting in a reduced tendency to leak, increased comfort and further may be used in connection with a wide variety of sizes of individuals. In addition, the invention provides a garment that can be lowered easily when changing clothes, checking for wetness or using bathroom facilities and then replaced.

10 Claims, 8 Drawing Figures

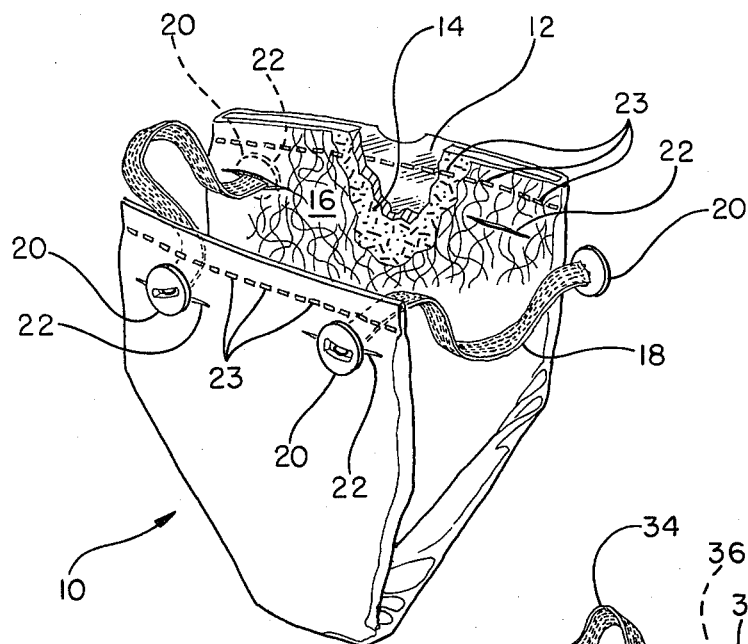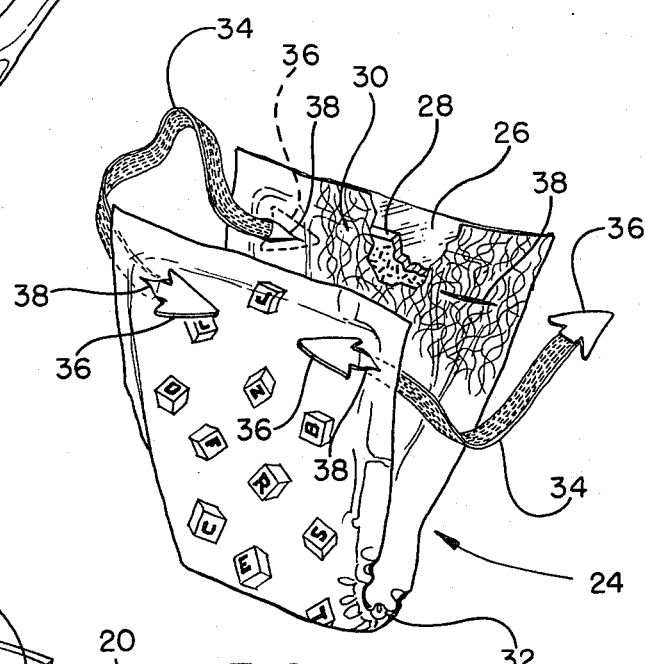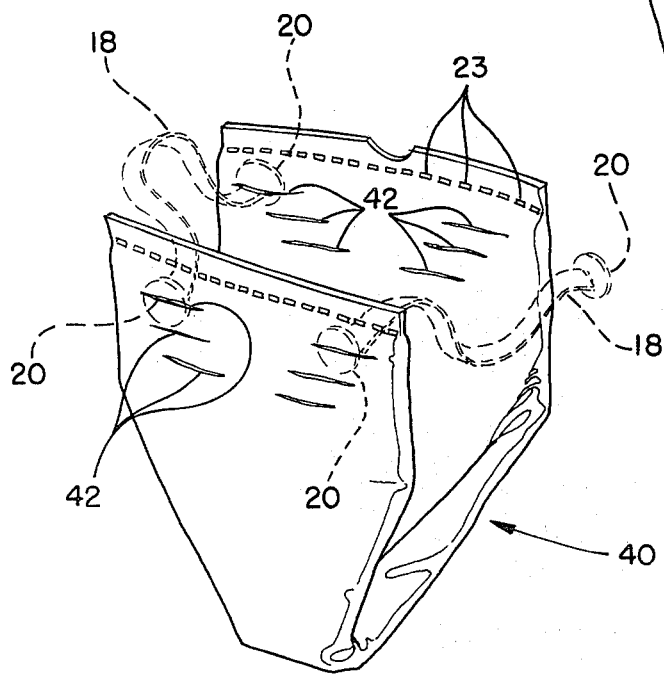

SELF-CENTERING MULTIPLE USE GARMENT SUSPENSION SYSTEM

BACKGROUND OF THE INVENTION

1. Field of the Invention

This invention relates to garments to be worn for sanitary purposes. In general, such garments include underwear, bathing suits, athletic supporters and the like, intended for multiple uses. Primarily, however, the field of the present invention is items that are intended for single use and are, therefore, disposable such as incontinent pads, disposable diapers, and the like.

Such disposable products, for the sake of economy, often result in a compromise between performance characteristics such as fit, comfort, and leakage and ability to be made at a cost consistent with disposability. In general, these products often comprise a rectangular absorbent material sandwiched between a liquid impervious backing and a facing material to provide containment of the absorbent material and a skin contacting surface. Particularly with disposable diapers intended for use with infants and children, it has generally been necessary to make garments of different dimensions to accommodate growth through the toddler years. This has necessitated capital equipment expenditures and is a source of inconvenience to the consumer who must make a selection between the sizes available. In particular, the present invention is directed to improvements in fit, comfort, and performance of such products.

2. Description of the Prior Art

Garments of the general type described are well-known. In particular, disposable diapers and incontinent garments are widely described in the patent literature and elsewhere. Among such publications are patents that relate to these classes of garments that are provided with various suspension or attaching means including those incorporating strips of elastic. For example, U.S. Pat. No. 3,800,796 to Jacob describes a disposable diaper having semielastic strip fasteners. U.S. Pat. No. 1,988,140 to Lowe describes a garment for more durable applications having a partially elasticized waist band. U.S. Pat. No. 2,408,723 to Arpin et al describes a similar garment. U.S. Pat. No. 3,452,753 to Sanford describes an incontinent device having multiple sets of elastic straps for maintaining the garment in position. U.S. Pat. No. 4,182,334 to Johnson describes in one embodiment a disposable diaper or incontinent pad with a suspension system including strips of elastic positioned so as to surround the thigh areas of the wearer.

Garments of the type described in the prior art as well as those which have been available commercially suffer from one or more of the following deficiencies: they are uncomfortable in that the elasticized portions tend to bind or otherwise irritate the wearer; they are size dependent and unable to accommodate a variety of wearers; they tend to sag in use resulting in significant leakage; they are expensive to manufacture; and they are not readily refastenable allowing a parent or person in charge of an incontinent, or the incontinent, to open and examine for wetness or to lower the garment when using bathroom facilities and refasten the garment.

SUMMARY

The present invention provides a combination of absorbent garment and suspension system that overcomes to a great degree the deficiencies in the prior art structures. In the combination of the present invention the garment is an absorbent material of generally rectangular construction. It may be woven or nonwoven cotton or other cloth-like material when the garment is intended for durable applications. It is contemplated, however, that most applications will include a disposable absorbent material having a nonpermeable backing, with an absorbent sheet of fluff, plied-up wadding, or the like on one side and sandwiched between a facing sheet which may be a nonwoven light-weight material such as spunbonded polypropylene, carded polyester or the like. While generally rectangular in shape, the absorbent garment portion may be folded in the crotch area to improve fit and comfort.

In cooperation with the absorbent garment, in accordance with the invention, two elastic straps are provided of a size and composition important to achieve the improved results. In general, the elastic straps will each be from 2 to 20 inches in length with a width of about $\frac{1}{2}$ inch to about 5 inches. It is important that the elastic straps have a structure that reduces the tendency to roll upon itself and produce tightness producing wearer discomfort. The elastic composition is also important in achieving the results of the present invention. The elastic must be soft, nonabrasive, and yield a high elongation (strain), preferably at least 200%, for a relatively low force (stress), preferably not in excess of 60 pounds, application. This is desirable for increased comfort and to minimize skin breakdown and/or circulatory problems. High strain increases the ability to accommodate a wide range of body sizes. One preferred material has an elongation of 335% for a stress application of 37.6 pounds of force. Also, it must be nonirritating and have the ability to withstand repeated use and, preferably, washing. Such compositions include, by way of example, an interwoven polyester/rubber fabric with a nylon fluff backing sold as Shelby Elastic K-78.

When combined, the pad and the straps produce, in use, an upward force that is exceptionally effective in maintaining the garment in place with a minimum degree of discomfort. This is achieved by positioning the elastic straps toward the hips of the wearer and at an angle in the range of from 25° to 45° from horizontal when viewed from a frontal position. The garment, preferably, has a width in the range of from 6 to 22 inches and a length in the range of from 10 to 34 inches. Also, preferably, the garment includes multiple attachment locations for achieving the strap orientation angle desired. Various attachment means may be used in conjunction with the garment strap such as, buttons, snaps, hooks, and the like.

The garment and suspension system of the invention thus achieve much improved fit and containment characteristics while avoiding the necessity for large, bulky, and expensive configurations previously used. In addition, the structure of the present invention will accommodate an extremely large variety of sizes and reduces the visibility of the garments avoiding a source of embarrassment, particularly with adult wearers. Finally, the garment and suspension system of the present invention are refastenable which is a particular advantage in nursing home and other incontinent treatment facilities where it is necessary to remove at least partially the garment to inspect for soiling and for changing or use of bathroom facilities. To a similar degree this is also an advantage with infant diapers of the present invention.

BRIEF DESCRIPTION OF THE DRAWINGS

FIG. 1 illustrates in schematic form, one embodiment of the garment and suspension system of the present invention;

FIG. 2 illustrates similarly a second embodiment;

FIG. 3 illustrates a third embodiment having adjustable strap positions;

DESCRIPTION OF THE PREFERRED EMBODIMENTS

Figure 4:
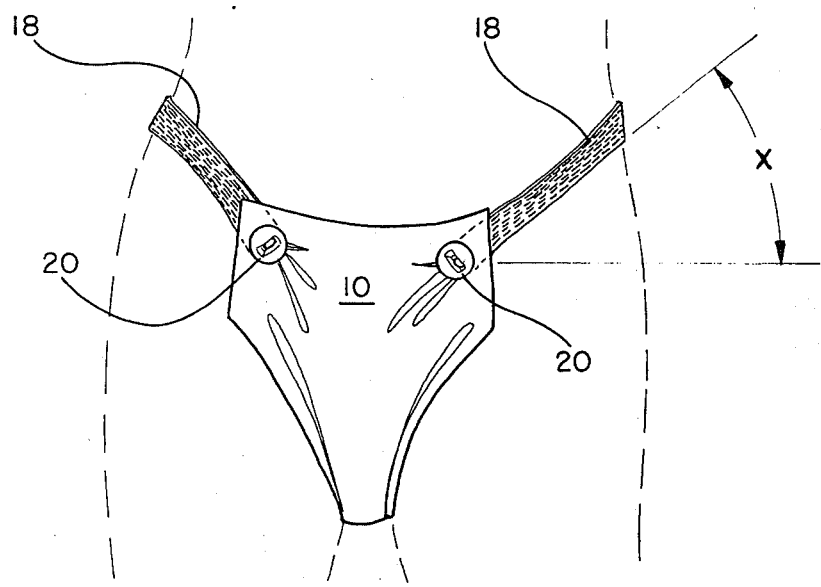
FIG. 4 illustrates the embodiment of FIG. 1 in use.

While the invention will be described in connection with preferred embodiments, it will be understood that it is not intended to limit the invention to those embodiments. On the contrary, it is intended to cover all alternatives, modifications and equivalents as may be included within the spirit and scope of the invention as defined by the appended claims.

Turning to FIG. 1, the garment and suspension system of the present invention are illustrated in the form of a disposable incontinent pad. As shown, the garment 10 includes impermeable backing 12, absorbent layer 14, and facing sheet 16. The backing sheet may be any of a wide variety of plastic materials conventionally used for backings for disposable diapers and incontinent pads, but, preferably, is matte embossed ¾ mil polypropylene. Such material is available from Edison Plastics under the designation PPLT Code 200 or from Clopay under the designation #SN278, Code 147. Other examples include polyethylene, poly ethyl methacrylate, ethylene vinyl acetate, and the like. The absorbent material may also be any of a wide variety of materials capable of absorbing a desired quantity of waste fluids. Examples include fluff, plied-up cellulose wadding, and other compositions such as mixtures of wood pulp and polypropylene as described in U.S. Pat. No. 4,100,324 to Anderson et al any of which may be used in combination with one or more of the newer so-called "superabsorbent" materials. The facing sheet also may be formed from a variety of materials, including many of the nonwoven fabrics such as, spunbonded polypropylene, bonded carded webs of polyester, rayon, or other materials, and needled or wet-formed nonwovens. Preferably, the facing material is of a sufficient strength to contain the absorbent material when wetted but of a relatively low basis weight, for example, in the range of from about 0.2 oz/yd$^2$ to 0.8 oz/yd$^2$. In a preferred embodiment the facing is spunbonded polypropylene of about 0.4 oz/yd$^2$ and envelops the entire pad and backing so that no film surface is available to contact the wearer's skin.

As shown, absorbent combination 10 is adapted for use in conjunction with a suspension system including straps 18. These straps are preferably ¼ inch to 5 inches in width, most preferably ¾ inch to 2 inches in width and have a length of between 2 to 20 inches, most preferably 5 to 11 inches depending upon the intended use. The straps are formed from a soft, nonabrasive, nonirritating elastic as described having high elongation, preferably at least 200%, for low force, preferably not in excess of 60 pounds, application.

The strap and the garment 10 are combined by means of fastening devices 20 in this case buttons, which are used in conjunction with fastening devices 22, in this case buttonholes, in each corner of pad 10. As illustrated in subsequent Figures, other fastening devices may be utilized as well including, snaps, hooks, hooks and loops, tapes, and the like. It is preferred, however, that the device utilized be reusable and capable of providing refastenability. For this reason, buttons, snaps and hooks are preferred. For improved integrity, lines of embossments 23 may be provided bonding layers 12, 14 and 16. Where thermoplastic materials are utilized, heat may also be used for stronger bonding.

Turning to FIG. 2, an alternative embodiment is illustrated showing a different diaper and suspension system constructed in accordance with the present invention. In similar manner, the device includes absorbent garment 24 having backing 26, absorbent medium 28, and facing sheet 30. In this embodiment gathered area 32 is provided in the crotch zone and backing 26 is decorated for attractiveness to children. Straps 34, in this case, are somewhat smaller dimensions and include a different fastening device combination of arrowhead shaped stiffened ends 36 and 38. Particularly with respect to infant diapers, the combination of the present invention allows a single size of absorbent garment 24 to fit a wide variety of sizes of children. A further significant advantage is that it also allows the diaper to be used with older children who may suffer from enuresis or daytime wetting problems.

FIG. 3 illustrates a further alternative structure. In this embodiment, the absorbent garment 40 includes several attachment apertures 42 arranged in rows extending toward the longitudinal center line and the crotch portion to allow adjustable fastening of straps. This provides for maximum flexibility in use so that the garment may be fitted in the preferred manner.

Turning to FIG. 4, the garment in use is shown illustrating how fitting is obtained and the straps maintained at an angle x in the range of from about 25° to 45° with horizontal in the standing position which results in the upward force that operates to maintain snug fit and position of the garment. Because of the nature of the suspension system, the garment is self-centering in that, regardless, of the method of donning it, it will tend to assume a centralized location on the wearer. This is because the elastic straps on either side are of equal length and exert equal force on the front and back edges of the pad.

Figure 5A:
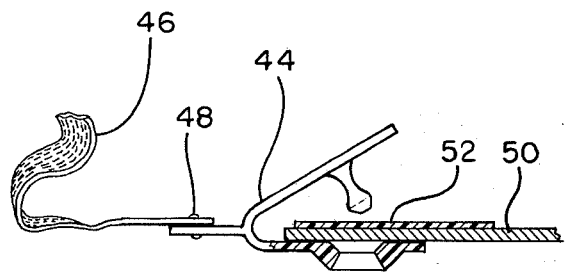
FIGS. 5 and 6 illustrate additional strap embodiments and associated fastening devices.
Figure 5B:
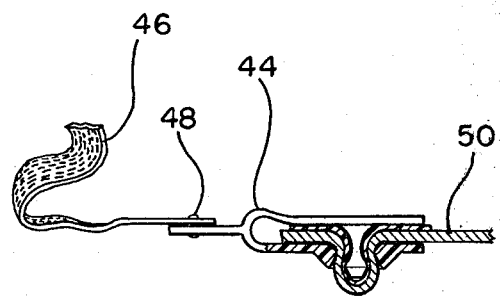
Figure 6A:
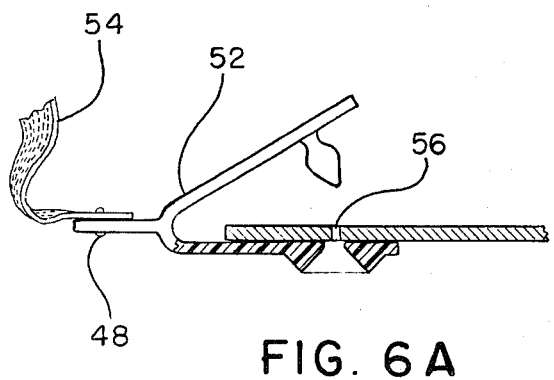
Figure 6B:
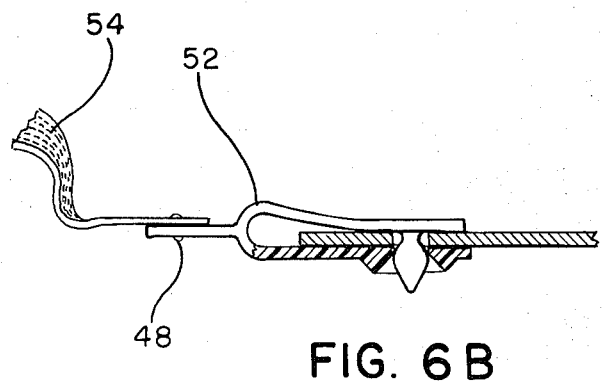

Turning to FIGS. 5 and 6, additional strap and attachment embodiments are shown, in the one case, FIGS. 5A and 5B, a clamping device 44 attached to the strap 46 by pin 48 can seize the garment corner 50 without necessitating apertures in the pad, itself. In such cases, corner 50 may be reinforced by applying coating 52 to produce secure attachment. In the other FIGS. 6A and 6B, a sharper clamp device 52 is attached to the elastic 54 which may fit through and form an aperture 56 while resisting removal. In both cases the clamps are formed as so called "living hinges" from plastics, such as polyester, polypropylene, polyethylene and the like.

EXAMPLE

In a preferred embodiment of the present invention, an incontinent garment is formed by placing an absorbent web of 160 g/yd$^2$ and 8 inches in width by 23 inches in length and formed from a mixture of 70% cellulose and 30% polypropylene fibers formed in accordance with U.S. Pat. No. 4,100,324 on a backing of 10 inches in width by 23 inches in length of ¾ mil polyethylene film. The film was wrapped about the web covering completely one surface and extending equally around the other surface leaving a middle portion exposed. This combination was wrapped completely with 0.4 oz/yd$^2$ spunbonded polypropylene 18 inches wide by 23 inches long and overlapped over the web. The overlapping portion was bonded along its length by polyester yarn coated with hotmelt adhesive. A tuck was formed in the crotch area by hotmelt adhesive, and slits were formed by cutting 1 inch from the ends and 1 inch from the sides at each corner. Elastic straps 8½ inches long with ⅜ inch buttons at each end were formed from Shelby K-78 and used to complete the garment and suspension structure as generally shown in FIG. 1.

In use the garment and suspension system of the present invention are economical because the straps may be used for multiple applications. Thus, they may be sold separately or provided as a single set in a box of many absorbent garments. Similarly, the absorbent sheets may be economically manufactured and sold at a price consistent with disposability. The improved fit and comfort obtained in accordance with the invention, thus provide a maximum degree of convenience while attaining a high degree of containment. The further advantages of refastenability and use over a wide size range add further improvement in accordance with the invention.

Thus, it is apparent, that there has been provided, in accordance with the invention, an improved garment and suspension system that fully satisfy the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A garment and suspension system therefor for use in absorbing and containing human waste excrement consisting essentially of,
    in combination, an absorbent pad having an absorbent medium contained between a liquid impervious backing and a facing material, said combination being of generally rectangular configuration and having a width in the range of from 6 to 22 inches and length in the range of from 10 to 34 inches with a releasable attachment means adjacent each corner thereof; and a pair of elastic straps formed from a soft, nonirritating, nonabrasive elastic having high strain and low stress properties with dimensions in the range of from 2 inches to 20 inches in length and ½ inch to 5 inches in width and having at each end fastening means for use in association with the attachment means of said absorbent sheet; wherein said garment and suspension system in use results in the straps extending toward the waist of the wearer and at an angle of from 25° to 45° with horizontal and provides a vertical vector of force to maintain the garment snugly in place.

2. The garment and suspension system of claim 1, wherein the straps are formed from interwoven polyester and rubber with a nylon fluff backing.

3. The garment and suspension system of claim 1 wherein the strap end fastening means comprise buttons and the garment fastening means comprise buttonholes.

4. The garment and suspension system of claim 1 wherein the strap end fastening means comprise arrowhead shaped stiffened ends and the garment fastening means comprise buttonholes.

5. The garment and suspension system of claim 1 wherein the strap end fastening means comprise living hinge clamps, and the garment fastening means comprises apertures.

6. The garment and suspension system of claim 1 wherein the strap end fastening means comprise living hinge clamps, and the garment fastening means comprises corner reinforcement.

7. The garment and suspension system of claim 1 wherein the garment contains multiple sets of corner releasable attachment means providing adjustable strap positions.

8. The garment and suspension system of claim 7 wherein the multiple sets comprise rows of buttonholes extending toward the longitudinal centerline and the crotch portion of the garment.

9. The garment and suspension system of claim 1 wherein the garment comprises an absorbent layer having on one side a liquid impervious backing and on the other a nonwoven facing which envelops both the absorbent layer and the backing.

10. The garment and suspension system of claim 1 wherein the absorbent layer comprises a mixture of wood pulp and polypropylene.

* * * * *

UNITED STATES PATENT AND TRADEMARK OFFICE
CERTIFICATE OF CORRECTION

PATENT NO. : B1 4,315,508
DATED : November 8, 1988
INVENTOR(S) : Martha E. Bolick It is certified that error appears in the above-identified patent and that said Letters Patent is hereby corrected as shown below:

Column 2, line 6, delete "portion" and substitute therefor --portions--.

Claim 15, column 2, line 21, after the fourth word "means" and prior to "and", insert the following words --,said loop means--.

Signed and Sealed this

Twenty-sixth Day of September, 1989

Attest:

DONALD J. QUIGG

Attesting Officer

Commissioner of Patents and Trademarks

REEXAMINATION CERTIFICATE (943rd)
United States Patent [19]

Bolick

[11] B1 4,315,508
[45] Certificate Issued  Nov. 8, 1988

[54] SELF-CENTERING MULTIPLE USE GARMENT SUSPENSION SYSTEM

[75] Inventor: Martha E. Bolick, Neenah, Wis.

[73] Assignee: Kimberly-Clark Corporation, Neenah, Wis.

Reexamination Request:
No. 90/001,174, Feb. 26, 1987

Reexamination Certificate for:
Patent No.: 4,315,508
Issued: Feb. 16, 1982
Appl. No.: 135,536
Filed: Mar. 31, 1980

[51] Int. Cl.⁴ ............................................. A61F 13/16
[52] U.S. Cl. ................................. 604/392; 604/370; 604/374; 604/385 R; 604/385 A
[58] Field of Search .................... 604/385.1, 385.2, 378, 604/370, 391, 392

[56] References Cited

U.S. PATENT DOCUMENTS

| | | | |
|---|---|---|---|
| Re. 21,624 | 11/1940 | Dann | 2/224 |
| 423,572 | 3/1890 | Preston | |
| 570,216 | 10/1896 | Ballard | |
| 676,636 | 6/1901 | Sonnehill | |
| 1,052,205 | 2/1913 | Baruch | |
| 1,104,674 | 7/1914 | Johnson | |
| 2,568,910 | 9/1951 | Condylis | 604/392 |
| 2,675,806 | 4/1954 | Bram | 128/288 |
| 2,695,025 | 11/1954 | Andrews | 128/287 |
| 3,025,856 | 3/1962 | Burwell et al. | 128/288 |
| 3,176,688 | 4/1965 | Tschappat | 604/386 |
| 3,313,300 | 4/1967 | Mathison et al. | 128/289 |
| 3,335,721 | 8/1967 | Gastwirth | 604/391 |
| 3,375,826 | 4/1968 | Field | 128/289 |
| 3,455,303 | 7/1969 | Wilson | 128/289 |
| 3,566,870 | 3/1971 | Benjamin | 128/289 |
| 3,771,524 | 11/1973 | Ralph | 128/287 |
| 3,825,006 | 7/1974 | Ralph | 128/287 |
| 4,182,334 | 1/1980 | Johnson | 604/385 A |
| 4,200,103 | 4/1980 | Black et al. | 604/370 |

FOREIGN PATENT DOCUMENTS

| | | |
|---|---|---|
| 88591 | 12/1921 | Fed. Rep. of Germany |
| 906365 | 3/1954 | Fed. Rep. of Germany |
| 1070779 | 12/1959 | Fed. Rep. of Germany |
| 252647 | 10/1948 | Switzerland |
| 318440 | 9/1929 | United Kingdom |
| 1144674 | 3/1969 | United Kingdom |
| 1560925 | 2/1980 | United Kingdom |

Primary Examiner—C. Fred Rosenbaum

[57] ABSTRACT

Suspension system intended primarily for disposable items such as incontinent pads, disposable diapers, and the like but having other uses as well. The garment is intended to be worn about the crotch area and generally is rectangular in shape although various fold configurations in the crotch area may be utilized for improved comfort and fit. The suspension system includes two elastic strips of generally similar construction and having dimensions elected in accordance with the invention to provide the self-centering and improved comfort and fit features. The ends of the elastic strips are provided with buttons or other fastening means intended to cooperate with means provided in the garment material so that, in use, the elastic provides a vertical vector of force maintaining the garment snugly in place. Preferably the straps in use form an angle in the range of from 25° to 45° from horizontal when viewed from a standing frontal position. Garments of the invention provide self-centering characteristics and close fit to the perineal area resulting in a reduced tendency to leak, increased comfort and further may be used in connection with a wide variety of sizes of individuals. In addition, the invention provides a garment that can be lowered easily when changing clothes, checking for wetness or using bathroom facilities and then replaced.

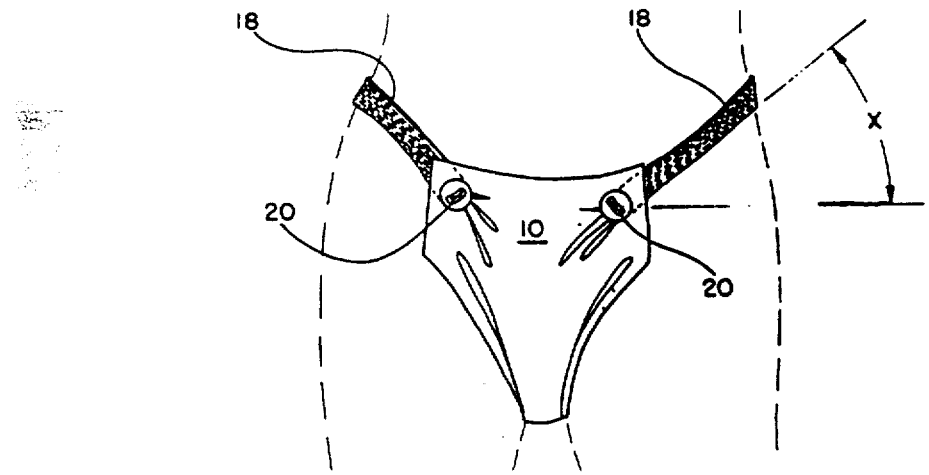

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–10 is confirmed.

New claims 11–21 are added and determined to be patentable.

*11. In combination, an incontinent garment and suspension system, consisting essentially of:*
  *a generally rectangular absorbent assembly including a liquid impervious backing, a liquid pervious facing, and a absorbent medium between said backing and said facing; said absorbent assembly having a width from 6 to 22 inches and a length from 10 to 34 inches, and a releasable attachment means adjacent each corner thereof, and*
  *a pair of elastic straps having at their respective ends fastening means being refastenable to said attachment means, and formed from a soft, nonirritating, nonabrasive elastic having high strain and low stress properties,*
  *each said elastic strap having a length from 2 to 20 inches and width from ¼ to 5 inches, and an elongation of at least about 200%, thereby accommodating various size users,*
  *an intermediate portion of each said elastic strap being extendable upwardly and outwardly from said absorbent assembly at an angle of from 25° to 45° with the horizontal to provide an upwardly and outwardly directed force vector, whereby said absorbent assembly is self-centering due to the oppositely applied upwardly and outwardly directed force vectors of said elastic straps.*

*12. The combination of claim 11 further comprising reinforcing means at the end portion of said absorbent assembly for providing additional integrity between said backing, said facing, and said absorbent medium.*

*13. The combination of claim 12 wherein said reinforcing means is a heat bond between said backing, said facing, and said absorbent medium.*

*14. The combination of claim 11 wherein said attachment means comprises hook means and said fastening means comprises loop means,*
  *said hook means and said loop means being removably engageable together, whereby said elastic straps are unfastenable and refastenable to said absorbent assembly.*

*15. The combination of claim 11 wherein said attachment means comprises loop means and said fastening means comprises hook means and said hook means being removably engageable together, whereby said elastic straps are unfastenable and refastenable to said absorbent assembly.*

*16. The combination of claim 11 wherein each said elastic strap has an elongation of about 335%.*

*17. The combination of claim 11 wherein said backing has a thickness of about ¼ mil and is made of a material selected from the group consisting of polypropylene, polyethylene, polyethyl methacrylate, and ethylene vinyl acetate.*

*18. The combination of claim 11 wherein said facing is a spunbonded polypropylene having a basis weight from about 0.2 ounces per sq. yd. to about 0.8 ounces per sq. yd.*

*19. The combination of claim 11 wherein said facing is a bonded carded web of nonwoven synthetic fibers.*

*20. The combination of claim 11 wherein said absorbent medium is a blend of wood pulp and polypropylene.*

*21. The combination of claim 11 wherein intermediate edge portions of said absorbent assembly are gathered together.*

* * * * *